United States Patent [19]

Carpentiere et al.

[11] Patent Number: 5,383,902
[45] Date of Patent: Jan. 24, 1995

[54] SURGICAL NEEDLE-SUTURE ATTACHMENT FOR CONTROLLED SUTURE RELEASE

[75] Inventors: Richard P. Carpentiere, Plantsville; Francis D. Colligan, Waterbury; Ronald H. Belcourt, Jr., Meriden; Giuseppe Giordano, Ansonia, all of Conn.

[73] Assignee: United States Surgical Corporation, Norwalk, Conn.

[21] Appl. No.: 71,653

[22] Filed: Jun. 2, 1993

[51] Int. Cl.⁶ ............................................. A61B 17/04
[52] U.S. Cl. ................................. 606/224; 606/222; 606/226
[58] Field of Search .............................. 606/222–226; 163/1, 5; 29/515, 517; 385/81, 84, 85, 87; 72/380, 470, 469, 446

[56] References Cited

U.S. PATENT DOCUMENTS

| | | |
|---|---|---|
| Re. 27,735 | 8/1973 | Shave et al. |
| Re. 31,084 | 11/1982 | Birks. |
| 1,558,037 | 10/1925 | Morton. |
| 1,578,543 | 3/1926 | Montgomery. |
| 2,067,568 | 1/1937 | Grunthal. |
| 2,205,893 | 6/1940 | Unger. |
| 2,411,079 | 11/1946 | Baule. |
| 2,620,028 | 12/1952 | Kohut. |
| 2,958,929 | 11/1960 | Vineberg et al. |
| 2,983,898 | 5/1961 | Kalmar et al. |
| 3,055,412 | 9/1962 | Dibner. |
| 3,611,551 | 10/1971 | Shave et al. |
| 3,643,327 | 2/1972 | Jackson. |
| 3,771,343 | 11/1973 | Dawson. |
| 3,890,975 | 6/1975 | McGregor. |
| 3,910,282 | 10/1975 | Messer et al. ........................ 606/226 |
| 3,910,282 | 10/1975 | Messer et al. |
| 3,924,630 | 12/1975 | Walldorf ............................. 606/226 |
| 3,963,031 | 6/1976 | Hunter. |

(List continued on next page.)

FOREIGN PATENT DOCUMENTS

| | | |
|---|---|---|
| 0249504 | 12/1987 | European Pat. Off. |
| 2459696 | 7/1975 | Germany ....................... 606/226 |
| 8715099 | 3/1988 | Germany. |
| 3805772 | 9/1988 | Germany. |
| 1526222 | 9/1978 | United Kingdom. |

Primary Examiner—Stephen C. Pellegrino
Assistant Examiner—Gary Jackson

[57] ABSTRACT

An apparatus is disclosed for attaching a surgical needle having a generally cylindrical end portion defining an elongated aperture having a generally circular cross-section and a suture having a generally elongated end portion of generally circular cross-section corresponding in dimension to the elongated aperture of the needle. The apparatus includes a pair of dies, each having a die face with an inner die surface portion. The inner die surface portion includes at least one generally planar crimping surface having an arcuate recess formed therein which extends along at least a portion of the planar crimping surface. The arcuate recess defines a material relief zone such that when the end portion of the suture is positioned within the aperture of the needle and the dies are positioned about the generally cylindrical end portion of the needle with the crimping surfaces generally facing the outer surface thereof, the application of an inward crimping force to the dies causes the dies to impact the needle and produce inward crimping forces on opposed sides of the needle end portion to attach the needle to the suture. The relief zones defined by the arcuate recesses receive and collect deformed material from the needle. According to the invention, the symmetry of the needle is maintained and the attachment is predictable and superior to those of the prior art. A surgical needle-suture combination having a controlled suture release is also disclosed as well as a method for forming such attachment is also disclosed.

32 Claims, 5 Drawing Sheets

U.S. PATENT DOCUMENTS

| | | |
|---|---|---|
| 3,972,219 | 8/1976 | Riehl . |
| 4,027,519 | 6/1977 | Backle . |
| 4,047,420 | 9/1977 | Edwards . |
| 4,054,144 | 10/1977 | Hoffman et al. . |
| 4,060,885 | 12/1977 | Hoffman et al. . |
| 4,067,224 | 1/1978 | Birks . |
| 4,072,041 | 2/1978 | Hoffman et al. . |
| 4,124,027 | 11/1978 | Boss . |
| 4,192,171 | 3/1980 | Hamilton . |
| 4,292,833 | 10/1981 | Lapp . |
| 4,361,948 | 12/1982 | Omata . |
| 4,498,222 | 2/1985 | Ono et al. . |
| 4,567,650 | 2/1986 | Balyasny et al. . |
| 4,672,734 | 6/1987 | Kawada . |
| 4,719,789 | 1/1988 | Wiebe et al. . |
| 4,722,384 | 2/1988 | Matsutani . |
| 4,799,311 | 1/1989 | Matsutani ................................. 163/1 |
| 4,805,292 | 2/1989 | Noguchi . |
| 4,890,614 | 2/1990 | Kawada . |
| 4,910,857 | 3/1990 | Tanaka ................................. 29/515 |
| 4,922,904 | 5/1990 | Uetake et al. . |
| 5,001,323 | 3/1991 | Matsutani et al. . |
| 5,012,066 | 4/1991 | Matsutani et al. . |
| 5,046,350 | 9/1991 | Proto et al. . |
| 5,084,963 | 2/1992 | Murray . |
| 5,099,676 | 3/1992 | Proto et al. . |
| 5,131,131 | 7/1992 | Proto et al. . |
| 5,168,619 | 12/1992 | Proto et al. . |
| 5,201,760 | 4/1993 | West ................................. 606/224 |
| 5,207,701 | 5/1993 | West ................................. 606/224 |
| 5,224,955 | 7/1993 | West ................................. 606/224 |
| 5,230,352 | 7/1993 | Putnam et al. ........................... 163/1 |

SURGICAL NEEDLE-SUTURE ATTACHMENT FOR CONTROLLED SUTURE RELEASE

BACKGROUND OF THE INVENTION

1. Field of the Invention

The present invention relates to the attachment of surgical sutures to surgical needles. In particular, the invention relates to a method and apparatus for the attachment of surgical needles to surgical sutures to provide a combined surgical needle-suture device possessing controlled suture release characteristics.

2. Description of Related Art

For many years, surgeons have employed needle-suture combinations in which a suture or ligature is attached to the shank end of a needle. Such needle-suture combinations are provided for a wide variety of monofilament and braided suture materials, both absorbable and no-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard needle attachment and removable or detachable needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture for various suture sizes are set forth in the United States Pharmacopeia (USP XXII 1990). The United States Pharmacopeia prescribes minimum individual pull-out forces and minimum average pull-out forces as measured for five needle-suture combinations. The minimum pull-out forces for both standard and removable needle-suture attachment set forth in the United States Pharmacopeia are hereby incorporated by reference.

One typical method for securing a suture to a needle involves providing a cylindrical recess in the shank end of a needle and securing a suture therein. For example U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess, see, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pretensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to the tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

Additional patents which describe the use of tubing to effect suture-needle attachment include U.S. Pat. Nos. 4,672,734 (forming needle from U-shaped metal plate around suture), 4,359,053 (silicone tubing), 3,814,296, 2,802,478 (chamfered tubing ends), 2,302,986, 2,240,330, 1,981,651 (needle and tubing screw threaded), 1,960,117, and 1,591,021.

Commonly assigned, U.S. Pat. No. 5,139,514 describes a combined surgical needle-suture device in which a surgical needle having a shank of reduced cross-section is attached to a suture through a shrinkable tubing, or micro-ferrule, which is fitted about the needle shank and a portion of the suture. Application of energy to the shrinkable tubing brings the tubing into engagement with both the needle shank and the suture. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-suture combinations and removable needle-suture combinations using a single attachment process and a common inventory of materials.

Minimum average pull-out forces for various sizes of combined surgical needle-suture devices are set forth in the United States Pharmacopeia and are as follows:

TABLE 1

| Suture Size | Average Pull-Out Force/Ounces |
| --- | --- |
| 8/0 | 2.39 |
| 7/0 | 3.20 |
| 6/0 | 5.92 |
| 5/0 | 7.97 |
| 4/0 | 15.97 |
| 3/0 | 23.63 |
| 2/0 | 38.80 |
| 1/0 | 52.89 |
| 1 | 63.48 |
| 2 and larger | 63.48 |

U.S. Pat. No. 3,875,946, referred to above, describes needle-suture combinations said to exhibit suture pull-out values that are substantially less than those given by the United States Pharmacopeia as set forth above. According to U.S. Pat. No. 3,875,946, employing the procedure described therein, combined surgical needle-suture devices can be obtained with the following average pull-out forces:

TABLE 2

| Suture Size | Average Pull-Out Force/Ounces |
| --- | --- |
| 8/0 | 1-2 |
| 7/0 | 1-3 |
| 6/0 | 2-5 |
| 5/0 | 3-7 |
| 4/0 | 3-15 |
| 3/0 | 3-23 |
| 2/0 | 3-26 |
| 1/0 | 10-26 |
| 1 | 10-26 |
| 2 and larger | 10-26 |

These pull-out forces are obtained by prestressing the suture, i.e., by applying tension to the suture after the tip of the suture has been inserted into an axial bore, or recess, formed in the blunt end of the needle and the needled suture has been swaged so that the force required to pull the suture out of the recess exceeds the minimum limits on needle attachment set forth in the United States Pharmacopeia but is less than the actual tensile strength of the suture used. As the suture is pulled from the needle during application of the tensioning force, the force required to move the end of the suture relative to the needle recess drops to the desired pull-out value, where the tension is released.

A prevailing controlled release needle-suture attachment is a swage or crimp attachment, such as described in the foregoing U.S. Pat. Nos. 3,890,975 and 3,980,177. Swaging dies for achieving removable needle attachment are disclosed in U.S. Pat. Nos. 4,060,885 and 4,072,041. Conventional crimp operations of the type disclosed in these patents are difficult to control. Usually a crimp is created between several dies which close to a fixed gap. Any variation in the crimping dies, the apparatus for closing the dies, the needle size, the hole size, or the suture size will increase variability of the needle suture attachment. Particularly with the manufacture of controlled release sutures, it heretofore has been critical to form the surgical needle to precise dimensions, i.e., the diameter of the needle and the size of the drilled hole may often have to be manufactured within a tolerance of ±0.0005 inches to achieve acceptable attachment. Similarly, the suture end to be attached to the needle has to be constructed within similar tight tolerances to assure that the combined tolerances of the suture and needle, when crimped with the crimping die apparatus result in a "pull-out" force within a narrowly defined range. These manufacturing demands result in increased manufacturing time and waste and, hence, increased cost to the manufacturer.

In addition, conventional crimping operations often distort the end of the needle thereby causing it to lose its symmetry. This is undesirable because it may result in an unacceptable pull-out force or increased trauma to tissue when the non-symmetrical needle is drawn through the tissue.

For example, one conventional crimping method requires that the back end of the needle be struck with two opposed dies. The needle is then rotated 90° and the dies are arranged to strike the needle a second time. In effect, the first strike changes a round hole into one of elliptical shape, i.e., major and minor axes. The act of rotating the needle 90° and repeating the operation to some extent completes the attachment. However, these procedures increase handling during manufacture and the likelihood that unacceptable attachment will be achieved. Indeed, rotating the suture and needle before the attachment is complete is likely to dislodge the suture tip in whole or part prior to completion of the attachment, resulting in unacceptable attachment. Moreover, multiple opposing die hits may produce a distorted needle end which results in corresponding asymmetry of tissue apertures and trauma during use.

In addition to size effects, the surface smoothness of the suture and the needle aperture, and the presence of any lubricants applied to either the suture or the needle may affect the resulting pull-out values. The conventional method of crimping, as described, underscores many of these parametric inconsistencies and necessarily utilizes multiple hits to overcome these process variabilities.

Commonly assigned U.S. Pat. Nos. 5,046,350 to Proto et al. and 5,099,676 to Proto et al. disclose crimping or swaging die configurations for attaching surgical needles and sutures. The split ring die disclosed in the U.S. Pat. No. 5,046,350 includes a relief zone defined between a pair of extensions. A needle positioned between a pair of the split ring dies is stricken by the extensions whereby the superfluous material caused by the swaging action collects within the relief zone. The novel configuration of the split ring die provides a more uniform swage while the needle retains its circular symmetry in the area of suture attachment.

U.S. Pat. No. 5,099,676 discloses a die featuring a novel clover leaf shape which is defined by a generally circular surface having a series of interconnected alternating individual convex and concave curved surfaces. The convex and concave surfaces permit needle material swaged during the crimping process to flow from the convex portions which perform the actual crimping action to the concave areas so as to collect within the concave portions. The clover leaf dies provide unique attachment of the suture components and also maintains the symmetry of the product.

The present invention is directed to a unique die arrangement and the swage formed thereby which overcome the inherent disadvantages associated with conventional crimping dies and processes, particularly applied to a suture needle to achieve removable needle-suture attachment. In accordance with the method and apparatus of the present invention, attachment is achieved while retaining the symmetry of the needle. A significant advantage of the method and apparatus of the present invention resides in the fact that the needle-suture components need not be manufactured to as strict tolerances in order to achieve consistent attachment and pull-out force. In addition, the method and apparatus for attaching needles to sutures requires less handling of the suture and needle and reduces process control requirements.

SUMMARY OF THE INVENTION

The present invention is directed to an apparatus for attaching a surgical needle having a generally cylindrical end portion defining an elongated aperture of generally circular cross-section and a suture having a generally elongated end portion of generally circular cross-section corresponding in dimension to the elongated aperture of the needle. The apparatus comprises a pair of dies with each die including a die face having an inner die surface portion. Each inner die surface portion includes at least one generally planar crimping surface having an arcuate recess formed therein which extends along at least a portion of the planar crimping surface. The arcuate recess defines a relief zone such that when the cylindrical end portion of the suture is positioned within the aperture of the needle and the dies are positioned about the generally cylindrical end portion of the needle with the crimping surfaces generally facing the outer surface thereof, applying inward crimping force to the dies causes the dies to impact the needle and produce inward crimping forces on opposed sides of the needle end portion to attach the needle to the suture whereby the arcuate recesses receive and collect deformed material from the needle while maintaining the same cross-sectional dimension of the needle in the portion crimped by the dies.

In the preferred embodiment, each planar crimping surface defines a plane which is angularly offset relative to a plane defined by the die face. The arcuate recess of each die is disposed along the approximate midline of the planar crimping surface and may extend for at least one-quarter the length of the crimping surface. Preferably, the arcuate recess defines a radius of curvature which remains constant throughout its length.

A pair of dies according to the present invention may be used to form detachable needle-suture combinations whereby the suture may be readily separated from the needle by a predetermined force by the user. In the alternative, the dies may form a non-detachable needle-suture combination whereby separation of the suture is accomplished by cutting.

The present invention is also directed to a method for attaching a surgical needle having a generally cylindrical outer portion and a blunt end with a substantially circular elongated aperture formed therein to a suture having an end portion suitably configured for insertion into the aperture. The method comprises the steps of providing a pair of dies with each die including a die face having an inner die surface portion for at least partial reception of the cylindrical outer portion of the needle, each die surface portion including at least one generally planar crimping surface having a generally arcuate-shaped concavity extending along a portion of the crimping surface, positioning the pair of dies adjacent the corresponding cylindrical portion of the needle with the inner die surface portions of the dies facing the generally cylindrical outer surface of the needle and the arcuate-shaped concavity extending along the direction of the needle portion which defines the elongated aperture and applying inward impact force to the dies to displace the dies toward each other causing the generally planar crimping surfaces of each die to engage the surface of the needle to thereby cause crimping of the needle and reduction of an average dimension of the aperture defined therein. The arcuate-shaped concavity of each said die is configured and dimensioned to permit deformed material of the needle to be received and collected therewithin so as to facilitate attachment of the needle and the suture.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
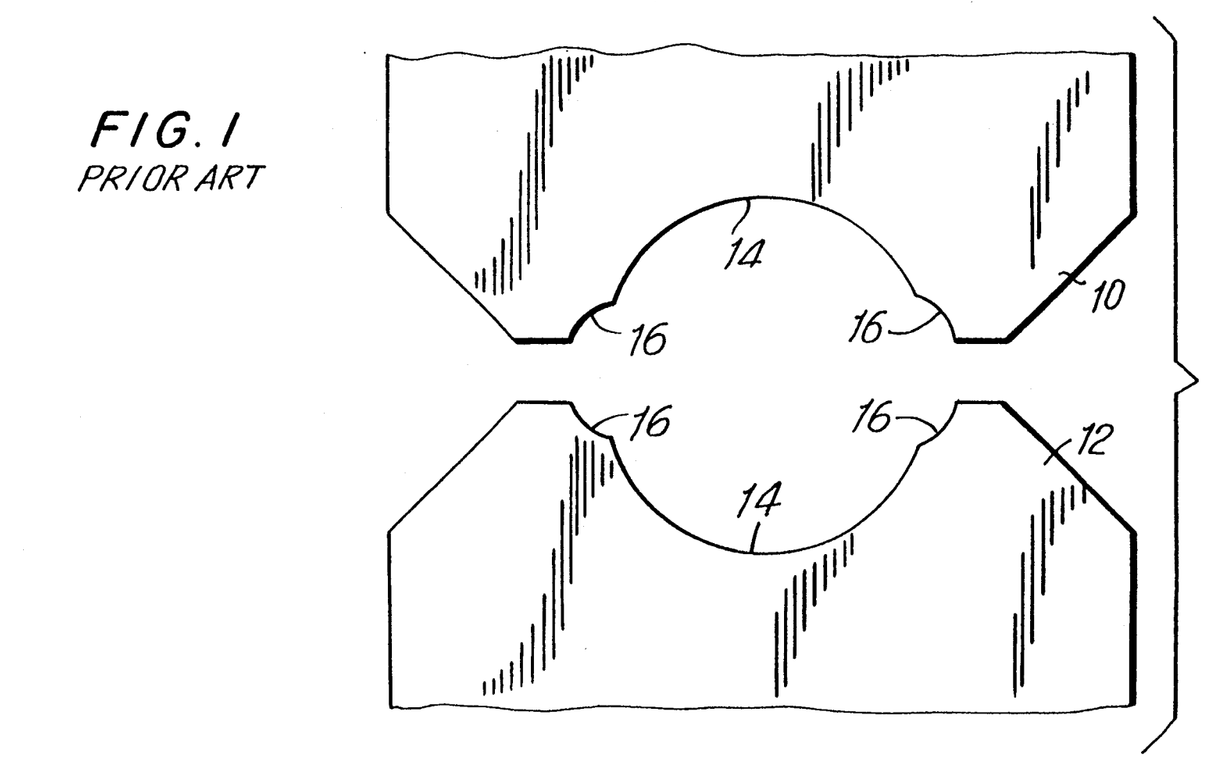
FIG. 1 is a plan view of a pair of conventional dual lap-overlap semicircular shaped dies.

Referring initially to FIG. 1, there is illustrated a pair of prior art dies 10, 12 of a type utilized to attach a suture to a surgical needle. Each die 10 has a working surface at 14 of generally semi-circular shape and adjacent arcuate corner portions 16 to receive limited amounts of excess needle material overflowing during the crimping process. The arcuate corner portions 16 are of lesser radii than the working surface and are not concentric therewith as shown.

To attach a needle to a suture, the dies are positioned within an apparatus as will be described hereinbelow. The apparatus is arranged to cause both dies to simultaneously move toward each other and strike a needle positioned between them. This causes the needle to become elliptical in cross-section and causes portions of the needle to deform into corner portions 16. Once the dies are impacted toward each other, they are separated and the needle is rotated 90°. The dies are then struck once again and the attachment is completed. In essence, the first strike causes the circular aperture in the needle to become elliptical. The second strike completes the attachment and reverses the distortion imparted to the needle. In certain instances additional hits are required to secure the suture to the needle. This procedure necessitates at least a dual step attachment which in turn requires additional time and labor.

Figure 2:
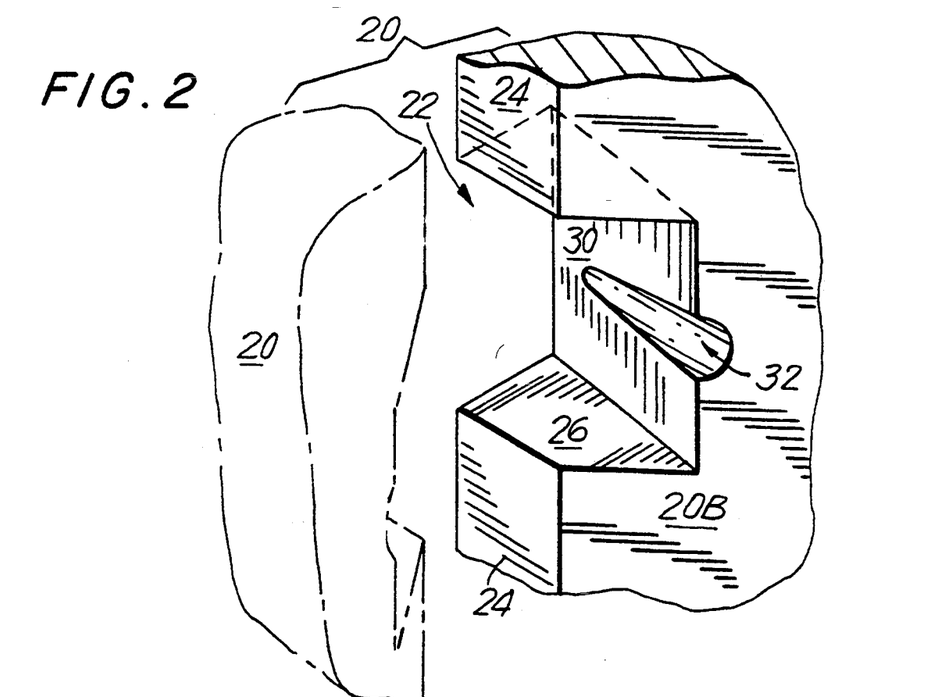
FIG. 2 is a perspective view of a swaging die constructed according to the present invention.
Figure 3:
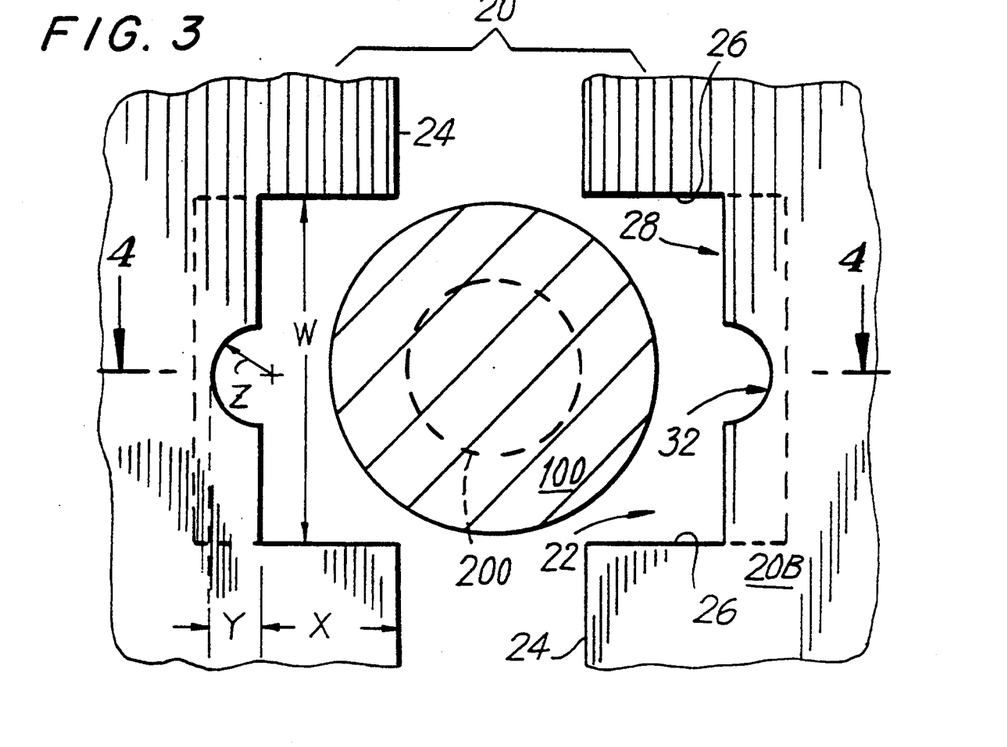
FIG. 3 is a rear axial view of a pair of dies constructed in accordance with the invention and shown with a needle positioned for attachment to a suture.
Figure 4:
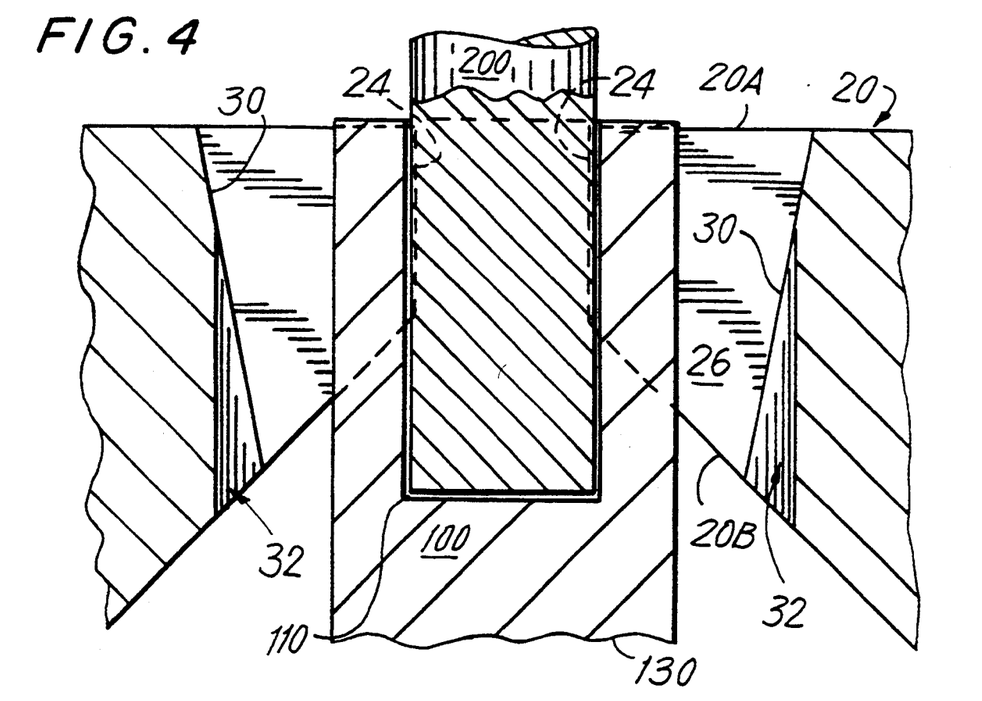
FIG. 4 is a cross-sectional view taken along lines 4—4 of FIG. 3.

Referring now to FIGS. 2–4 there is illustrated a pair of dies 20 constructed according to the present invention. Each die 20 is configured to have an inner cavity 22 (FIGS. 2 and 3) which, when combined with the other die of the pair, forms a generally rectangular opening for reception of an end of a needle to be swaged. The particular arrangement of the pair of dies 20 is best depicted in the axial view of FIG. 3 in which the dies are shown with a needle 100 therebetween in a position to be attached to a suture 200 (shown in phantom) and the cross-sectional view of FIG. 4 which is taken along lines 4–4 of FIG. 3. In FIGS. 2–4, the dies 20 are shown separated from each other in position prior to impact on a surgical needle 100 having an aperture 110 in which the end portion of suture 200 is positioned (See FIG. 4).

Each die includes a die face 24, a pair of inner walls 26 perpendicular to the die face 24, and an inner die surface portion 28. The dies 20 also have a front surface 20A and an angled rear surface 20B (see FIGS. 2 and 4). The inner die surfaces 28 each include a substantially planar crimping or swaging surface 30. Swaging surfaces 30 are each angled relative to a plane defined by the die face 24. In particular, as shown in FIG. 4, swaging surfaces 30 gradually taper radially inwardly, relative to needle 100 disposed within the dies, going from the front surface 20A of die 20 to the rear surface 20B of the die 20.

The cross-sectional view of FIG. 4 illustrates the tapering feature of swaging surfaces 30 in greater detail. As shown in the FIG., each swaging surface 30 of a single die 20 defines a plane which is oriented at an angle relative to a plane defined by die face 24. As will become appreciated from the description provided hereinbelow, such orientation of swaging surfaces 30 produces, opposed tapered surfaces on the needle end. The angle defined by swaging surfaces 30 relative to their respective die faces 24 may range from about 6° to about 15°. In a preferred embodiment, this angle is about 11°.

Referring again to FIGS. 2–4, inner die surface portion 28 also includes an arcuate-shaped concavity or recess 32. Recesses 32 are formed in swaging surfaces 30 and may extend from approximately ¼ of the length of swaging surface 30 to approximately ¾ the length of the surface. Recesses 32 define material relief zones to receive needle material displaced by the die 20 when a pair of dies are caused to strike a needle positioned within the generally rectangular-shaped cavity as described above. Recesses 32 are preferably generally arcuate in shape and define a radius of curvature which is generally constant throughout its length. The axis defined by each arcuate recess 32 of die 20 is substantially parallel to the plane defined by its respective die face 24. However, due to the tapering configuration of swaging surface 30 relative to die face 24, the depth of recess 32 gradually decreases towards the front end portion 20A of the die as best shown in FIGS. 2 and 4. Recesses 32 are each preferably disposed along the midline of swaging surface 30.

Figure 5:
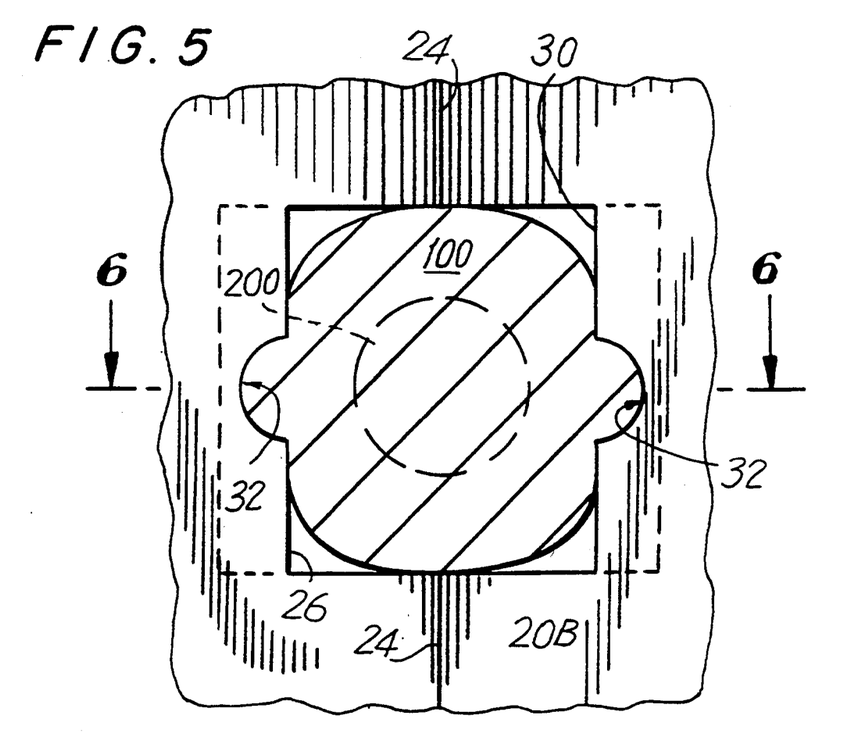
FIG. 5 is a rear axial view similar to the view of FIG. 3 illustrating the dies in a closed position engaging the needle end.
Figure 6:
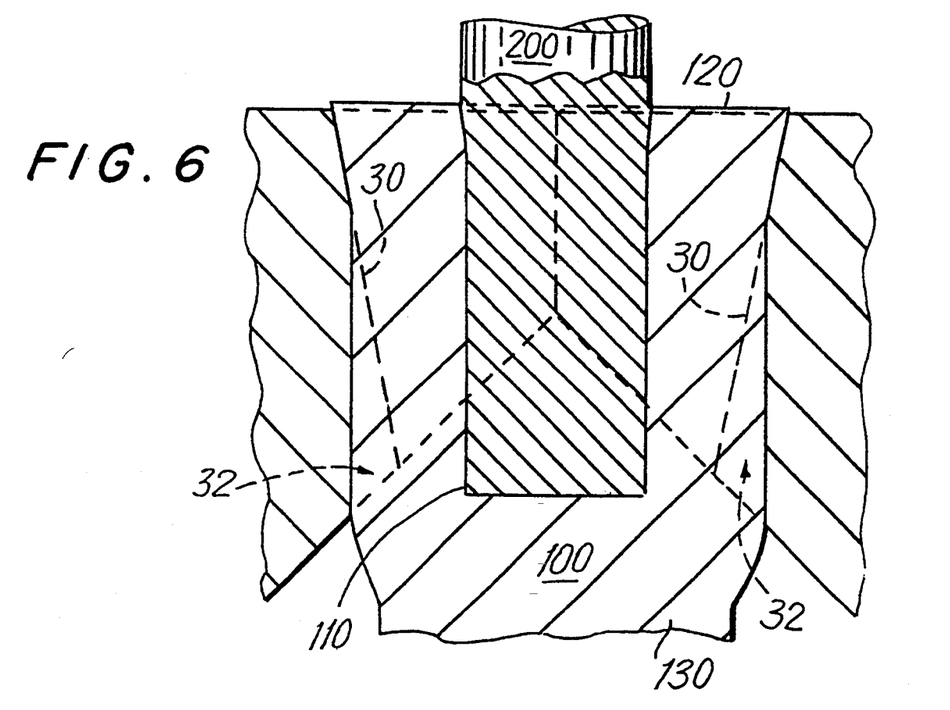
FIG. 6 is a cross-sectional view taken along lines 6—6 of FIG. 5.

FIGS. 5–6 illustrate the swaging effect dies 20 produce on the drilled needle end. During the crimping process, the dies 20 are moved towards each other until die faces 24 meet, whereby the swaging surfaces 30 strike the drilled or blunt end portion of needle 100. The needle material which is engaged by swaging surfaces 30 accumulates by the swaging action into the relief zone provided by recess 32. Simultaneously therewith, the apertured portion of the needle will be effectively crimped and attached to the suture by the physical reduction of the dimension of the aperture surrounding the suture.

Advantageously, the dies of the present invention require only one strike or "hit" to effect attachment of the suture components, thus, eliminating the double-hit method along with its inherent disadvantages. Further, the dies are capable of consistently producing detachable needle-suture combinations having pull-out values within the ranges set forth in U.S. Pharmacopeia. A further significant advantage of the present die resides in the fact that its particular configuration reduces the criticality of manufacturing the suture components to relatively strict tolerances even when detachable needle-suture attachment is the objective. For example, with conventional crimping procedures for producing detachable needle-suture combinations the suture and needle components often need to be manufactured to a ±0.0005 inch tolerance in order to achieve proper detachable needle attachment. However, with the dies 20 of the present invention, manufacturing tolerances need to be held only to ±0.0025 inch to provide consistent acceptable detachable needle-suture combinations. This is due to the nature of the crimp formed in the blunt end of the needle. In particular, the depth of the crimp is sufficient to cause the swaged portion of the needle to securely contact and engage the suture even if precise manufacturing tolerances are not met.

Similarly, with conventional crimping dies and processes, the "ovality" of a suture may present additional difficulties regarding suture attachment. Ovality is a term of art that refers to the degree in which the cross-sectional dimension of the suture varies from an exact circular configuration. In known crimping processes, the suture must approach a near circular cross-section to achieve proper removable needle suture attachment. This is disadvantageous in that the extra manufacturing processes required to obtain a substantially circular suture are costly and time consuming. With the dies of the present invention, the ovality of the suture is not as critical as a parameter in achieving acceptable suture attachment since the depth of the crimp formed by the dies is sufficient to securely engage the suture and compensates for any variation in the suture dimensions.

In the preferred crimping or swaging method, the needle 100 and suture 200 is positioned within the dies in the manner shown in FIG. 4, i.e., the blunt end surface 120 of needle 100 is aligned with the front end 20A of the dies as shown with the suture 200 inserted within aperture 102 of the needle. Consequently, with this particular positioning of the needle 100 within dies 20, the greatest depth of the crimp caused by the swaging surfaces 30 is provided away from the blunt needle end 120 towards the needle point 130. Accordingly, the tapered surfaces formed on the needle taper inwardly towards the needle point 130.

The particular dimensions of die 20 may be modified to accommodate different sized surgical needles. Referring to FIG. 3, dimension "W" of die 20 may be increased or decreased depending on the diameter of the needle end to be received within the die. Similarly, dimension "X" which indicates the depth of the die may also be modified for a particular needle size. Further, radius "Z" which indicates the dimension of the radius of curvature of recess 32 may also be varied to accommodate alternative dimensioned needle and suture components. Dimension Y which indicates the maximum depth of recess 32 and which is a function of radius "Z" may also be varied. The following chart indicates proposed die parameters for various sized surgical needles.

TABLE

| Needle Size | Dim. W | Dim. X | Dim. Y | Radius Z |
| --- | --- | --- | --- | --- |
| .050 | .0540 | .0140 | .0070 | .0085 |
| .044 | .0475 | .0120 | .0062 | .0075 |
| .039 | .0420 | .0095 | .0055 | .0066 |
| .034 | .0365 | .0090 | .0048 | .0058 |
| .032 | .0340 | .0085 | .0044 | .0054 |
| .030 | .0320 | .0060 | .0042 | .0051 |
| .028 | .0300 | .0050 | .0039 | .0048 |
| .026 | .0280 | .0045 | .0036 | .0044 |
| .024 | .0260 | .0040 | .0034 | .0040 |
| .022 | .0240 | .0036 | .0031 | .0038 |
| .020 | .0220 | .0030 | .0028 | .0034 |

The foregoing table illustrates the dimensional characteristics required for detachably connecting a needle of a particular dimension to a suture with the die of the present invention. The table is intended to be used only as a guide since the particular dimensions of the die may vary depending on the type and size of the suture being attached as well as the presence of lubricants, etc. One skilled in the art may readily determine appropriate dimensions for the die so as to achieve the objectives of the present invention. Further, it is to be noted that the angular orientation of swaging surfaces may be altered to achieve other desired results as well.

Preferably, the die of the present invention is configured in a manner such that the needle is detachably attached to the suture so as to be readily separated by a quick tug provided by the surgeon. However, it is entirely within the scope of the present invention to modify the die such that the needle is attached with greater pull-out so as to provide a "non-detachable" suture, in which case the suture may be separated from the needle in a more conventional manner, as by cutting with scissors or a scalpel.

Figure 7:
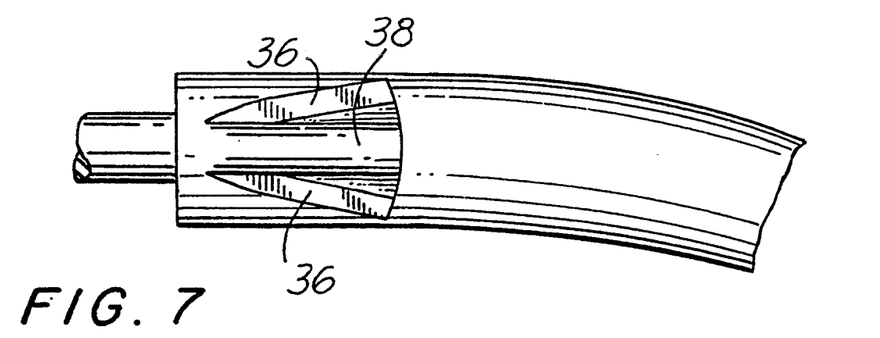
FIG. 7 is a plan view of the "crimped" needle illustrating the effects of the dies of the present invention on the needle surface.
Figure 8:
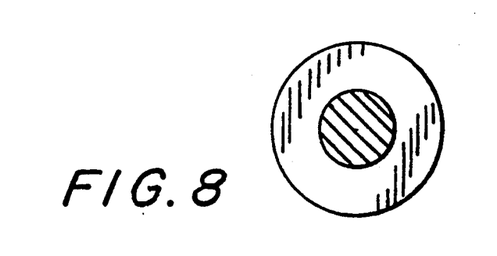
FIG. 8 is an end view of a needle crimped by the dies of the present invention.

Referring now to FIGS. 7 and 8, the drawings illustrate the configuration of the needle after the crimping process. The dies form a generally arrow-shaped impression on the needle surface. The swaging surfaces of the die produce tapered surfaces 36 on the needle. The arcuate raised portion 38 present on the needle end reflects the relief zone 32 of the die where the material overflow is received during swaging. As shown in the axial view of FIG. 8, needle-suture attachment is achieved while maintaining the general symmetry of the needle A with relatively insignificant surface distortion except for the minor impression formed on the surface. Thus, the needle retains its general circular symmetry in the area of suture attachment which thereby minimizes tissue trauma during the suturing process.

Figure 9:
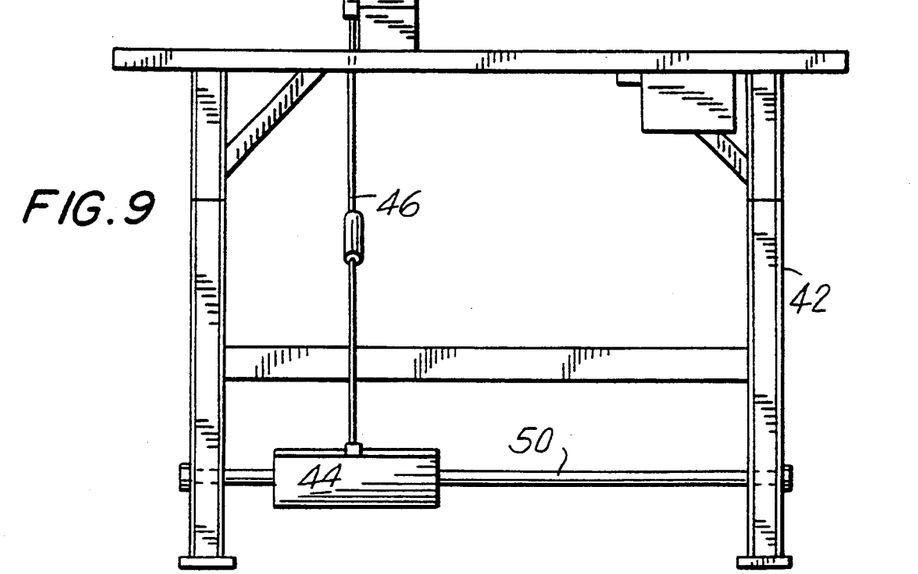
FIG. 9 is a front view of an apparatus with which the dies constructed according to the present invention may be utilized to attach a suture to a needle by crimping.
Figures 10, 11, 12:
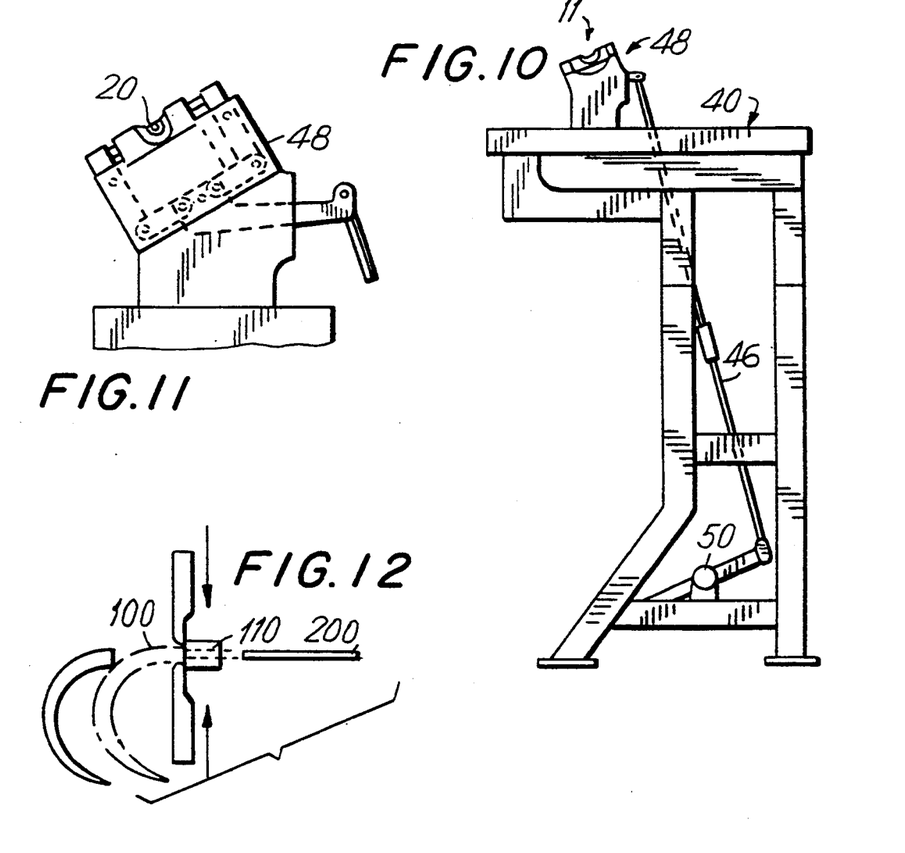
FIG. 10 is a side view of the apparatus shown in FIG. 9.
FIG. 11 is an exploded view illustrating the dies of the present invention mounted in the apparatus of FIG. 9 for attaching a suture to a needle.
FIG. 12 is an exploded side view of a pair of dies constructed according to the present invention positioned to attach a suture to a curved surgical needle.

Referring now to FIGS. 9 and 10 there is shown an exemplary apparatus 40 on which sutures may be attached to needles utilizing a pair of dies of the present invention. The apparatus 40 shown in manufactured and marketed as model 6A Suture Attaching Machine by B. G. Sulzle, Inc., Syracuse, N.Y. Other comparable machines suitable for attaching sutures may be utilized with the dies of the present invention.

The suture attaching machine 40 as illustrated in FIG. 9 includes a table 42 having treadle 44 which is foot operated and connected via treadle rod 46 to suture press 48. The treadle 44 is mounted for pivotal movement on pivot rod 50.

Referring now to FIG. 11 there is shown a side view of the apparatus shown in FIG. 10. The suture press 48 is encircled and is shown in enlarged form in FIG. 11. As can be seen in FIG. 11, the pair of dies 20 which are constructed according to the invention are positioned within the jaws of the suture press 48 and arranged to be stricken against a needle 100 with the suture 200 in position as shown in FIG. 12.

The needle 100 shown in FIG. 12 is of a curved type having a straight rear end portion which defines an elongated aperture 110 dimensioned for reception and attachment to an appropriately sized suture 200. The needle 100 is supported on a guide support having a "V shaped" guide channel which positively determines and positions the needle location and orientation as shown. Thereafter, appropriate adjustments are made to predetermine the strike force to be transmitted to the needle and suture as may be appropriately calculated to obtain a predetermined pull-out force. The treadle is depressed to cause the dies to strike the needle.

An alternative apparatus for attaching surgical sutures to needles is disclosed in commonly assigned U.S. patent application Ser. No. 07/959,114, filed Oct. 9, 1992, the contents of which are incorporated herein by reference. This apparatus includes a frame for positioning and maintaining the needle while the suture is being attached and a die system which selectively impacts the needle to secure the needle thereto. The die system may be modified to incorporate the novel dies of the present invention.

It will be readily appreciated that the dies of the present invention are particularly advantageous in that many types of sutures may be readily attached to needles having an aperture in their blunt end, i.e., drilled end needles. Further, single strike force is utilized thereby avoiding the need to provide "double-hit" attachment as necessary with prior art dies. This procedure provides a suture having a needle which is symmetrical and unaffected by the distorting forces provided by dies and procedures of the prior art. Moreover, the single-hit attachment procedure provides consistent and controlled attachment of the suture and the needle which additionally reduces the time and effort to complete the attachment. Die life is increased, rejected needle/suture attachments are reduced, and attachment time is reduced. As a result the cost of producing a surgical suture is sizably reduced.

The swaging dies of the present invention may be utilized with all types of needles such as curved needles, straight needles, or the like, provided they have an elongated aperture on their end portion for receiving the suture. Sutures usable with the present invention include silk, nylon, linen, cotton, polyester, polypropylene, stainless steel, natural materials such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable. The dies of the present invention are preferably constructed of a hardened material such as tungsten carbide. However, it should be understood that all materials suitable for such die construction may be used, provided the geometric and configurational parameters taught by the present invention are met.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for attaching a surgical needle to a suture, the needle having a generally cylindrical outer portion and a blunt end with a substantially circular elongated aperture formed therein, the suture having an end portion suitably configured for insertion into the aperture, comprising:

providing a pair of dies, each die including a die face having an inner die surface portion for at least partial reception of the cylindrical outer portion of the needle, each die surface portion including at least one generally planar crimping surface having a generally arcuate-shaped concavity extending along a portion of said crimping surface;

positioning said pair of dies adjacent the corresponding cylindrical portion of the needle with said inner die surface portions of said dies facing the generally cylindrical outer surface of the needle, said generally planar surfaces of said dies angularly offset relative to the longitudinal axis of the elongated aperture of the needle and said generally planar surfaces of said dies and said arcuate-shaped concavity extending along the direction of the needle portion which defines the elongated aperture; and applying inward impact force to said dies to displace said dies toward each other causing said generally planar crimping surfaces of each die to engage the surface of the needle to thereby cause crimping of said needle at an angle offset relative to the longitudinal axis of the elongated aperture of the needle and reduction of an average dimension of the aperture defined therein, whereby said arcuate-shaped concavity of each said die is configured and dimensioned to permit deformed material of the needle to be received and collected therewithin so as to facilitate attachment of the needle and the suture.

2. The method according to claim 1 the step of positioning said pair of dies further comprises positioning said dies such that planes defined by said die faces are generally parallel with respect to each other and with a longitudinal axis defined by the elongated aperture of the needle.

3. The method according to claim 2 wherein the step of providing said dies further comprises forming each said a least one crimping surface such that a plane defined thereby is angularly offset relative to the plane defined by said die face.

4. The method according to claim 3 wherein the step of providing said dies further comprises dimensioning each said arcuate-shaped concavity such that it extend substantially along a midline of said at least one crimping surface.

5. The method according to claim 4 wherein the step of providing said dies further comprises dimensioning each said arcuate-shaped concavity such that the radius of curvature defined thereby is constant throughout its length.

6. The method according to claim 5 wherein the step of providing said dies comprising dimensioning each said arcuate-shaped concavity such that the axis defined thereby is substantially parallel to said die face.

7. The method according to claim 6 wherein each said at least one crimping surface is comprised of hardened material.

8. The method according to claim 7 wherein said hardened material is tungsten carbide.

9. The method according to claim 8 wherein said needle is manufactured of stainless steel.

10. The method according to claim 1 wherein the suture is detachably attached to the needle whereby the suture may be readily separated from the needle by a relatively sudden predetermined force provided by the user.

11. The method according to claim 1 wherein the suture is non-detachably attached to the needle whereby separation of the suture from the needle may be accomplished by cutting.

12. The method of claim 1 wherein said arcuate raised portion extends from approximately $\frac{1}{4}$ to $\frac{3}{4}$ the length of the generally planar crimping surface.

13. The method of claim 2 wherein the angle defined between each said die face and the generally planar crimping surface is in the range of from about 6° to 15°.

14. The method of claim 2 wherein the angle defined between each said die face and the generally planar crimping surface is about 11°.

15. A needle-suture combination, which comprises:
a) a surgical needle including a sharp end and a blunt end, said blunt end defining an elongated aperture therein;
b) a suture having a generally elongated end portion which is positioned within said elongated aperture of said needle; and
c) a portion of said blunt end swaged to cause attachment of said needle to said suture, said swaged portion including at least one generally planar surface which is angularly offset relative to a longitudinal axis defined by said elongated aperture of said needle and at least one substantially arcuate raised portion, said swaged portion having substantially the same cross-sectional character as the remaining portion of said blunt end.

16. The needle-suture combination according to claim 15 wherein said elongated aperture of said needle has a generally circular cross-section.

17. The needle-suture combination according to claim 16 wherein said elongated end portion of said suture has a circular cross-section corresponding in dimension to said elongated aperture of said needle.

18. The needle-suture combination according to claim 17 wherein said at least one generally planar surface defines a plane which is angularly offset relative to a longitudinal axis defined by said elongated aperture of said needle.

19. The needle-suture combination according to claim 18 wherein said at least one substantially arcuate raised portion extends substantially along the midline of said at least one generally planar surface.

20. The needle-suture combination according to claim 19 wherein said swaged portion of said needle comprises two opposed generally planar surfaces, each said generally planar surface having one said substantially arcuate raised portion disposed along said midline thereof.

21. The needle-suture combination according to claim 20 wherein said suture is detachably attached to said needle whereby said suture may be readily separated from said needle by a predetermined force provided by a user.

22. The needle-suture combination according to claim 20 wherein said suture is non-detachably attached to said needle whereby separation of said suture from said needle may be accomplished by cutting.

23. The needle-suture combination according to claim 15 wherein said suture is made of at least one of suture material such as silk, nylon, linen, cotton, polyester, stainless steel, polypropylene, nature materials such as catgut, and synthetic polymers having glycolic acid ester linkages subject to hydrolytic degradation to nontoxic, tissue compatible absorbable components, including polyglycolic acid.

24. The needle-suture combination according to claim 15 wherein said needle is manufactured of stainless steel.

25. A needle-suture combination, which comprises:
a) a surgical needle including a sharp end and a blunt end, said blunt end defining an elongated aperture therein;
b) a suture having a generally elongated end portion which is positioned within said elongated aperture of said needle; and
c) a portion of said blunt end swaged to cause attachment of said needle to said suture, said swaged portion including two opposed generally planar surfaces angularly offset relative to a longitudinal axis defined by said elongated aperture of said needle, each said generally planar surface having a substantially arcuate raised portion disposed along the midline of such surface.

26. The needle-suture combination according to claim 25 wherein said elongated aperture of said needle has a generally circular cross-section.

27. The needle-suture combination according to claim 26 wherein said elongated end portion of said suture has a circular cross-section corresponding in dimension to said elongated aperture of said needle.

28. The needle-suture combination according to claim 25 wherein said suture is detachably attached to said needle whereby said suture may be readily separated from said needle by a predetermined force provided by a user.

29. The needle-suture combination according to claim 25 wherein said suture is non-detachably attached to said needle whereby separation of said suture from said needle may be accomplished by cutting.

30. The needle-suture combination according to claim 25 wherein said suture is made of at least one of suture material such as silk, nylon, linen, cotton, polyester, stainless steel, polypropylene, nature materials such as catgut, and synthetic polymers having glycolic acid ester linkages subject to hydrolytic degradation to nontoxic, tissue compatible absorbable components, including polyglycolic acid.

31. The needle-suture combination according to claim 25 wherein said needle is manufactured of stainless steel.

32. The needle-suture combination according to claim 25 wherein said arcuate raised portion extends from approximately $\frac{1}{4}$ to $\frac{3}{4}$ the length of the generally planar surface.

* * * * *